United States Patent
Baxter et al.

(10) Patent No.: US 8,622,992 B2
(45) Date of Patent: Jan. 7, 2014

(54) DEVICES AND METHODS FOR PERFUSION THERAPY

(76) Inventors: Blaise Baxter, Signal Mountain, TN (US); Thomas Devlin, Signal Mountain, TN (US); Christian Devlin, Signal Mountain, TN (US)

(*) Notice: Subject to any disclaimer, the term of this patent is extended or adjusted under 35 U.S.C. 154(b) by 738 days.

(21) Appl. No.: 12/702,245

(22) Filed: Feb. 8, 2010

(65) Prior Publication Data

US 2010/0204634 A1 Aug. 12, 2010

Related U.S. Application Data (60) Provisional application No. 61/150,783, filed on Feb. 8, 2009, provisional application No. 61/263,790, filed on Nov. 23, 2009.

(51) Int. Cl.
*A61M 31/00* (2006.01)

(52) U.S. Cl.
USPC .............. 604/508; 604/96.01; 606/198

(58) Field of Classification Search
USPC ........... 604/8, 9, 507–509; 606/142, 194, 198
See application file for complete search history.

(56) References Cited

U.S. PATENT DOCUMENTS

| | | | |
|---|---|---|---|
| 5,626,564 A | 5/1997 | Zhan et al. | |
| 5,830,181 A | 11/1998 | Thornton | |
| 6,436,087 B1 * | 8/2002 | Lewis et al. | 604/508 |
| 6,537,241 B1 * | 3/2003 | Odland | 604/9 |
| 6,602,241 B2 | 8/2003 | Makower | |
| 6,605,074 B2 | 8/2003 | Zadno-Azizi | |
| 6,790,204 B2 | 9/2004 | Zadno-Azizi | |
| 6,945,978 B1 * | 9/2005 | Hyde | 606/142 |
| 7,235,264 B2 | 6/2007 | Neu | |
| 7,427,287 B2 | 9/2008 | Turovskiy | |
| 7,700,135 B2 | 4/2010 | Neu | |
| 2005/0288631 A1 | 12/2005 | Lewis | |
| 2006/0149187 A1 | 7/2006 | Bertolero | |
| 2008/0058758 A1 | 3/2008 | Ranchod et al. | |
| 2008/0058759 A1 | 3/2008 | Makower | |
| 2008/0200946 A1 | 8/2008 | Braun | |

FOREIGN PATENT DOCUMENTS

| | | |
|---|---|---|
| WO | PCT/US2008/053343 | 8/2008 |
| WO | PCT/US2009/039967 | 10/2009 |

OTHER PUBLICATIONS

International Preliminary Report on Patentability & Transmittal of the Same of the PCT Counterpart (PCT/US2010/23525), dated Aug. 9, 2011—4 pages.

\* cited by examiner

*Primary Examiner* — Melanie Hand
(74) *Attorney, Agent, or Firm* — Soody Tronson Law Group, P.C.

(57) ABSTRACT

Devices, methods, and assemblies for perfusion therapy including cerebral perfusion therapy such as those for use in the treatment of acute ischemic stroke. The treatment includes delivery of blood to or about the vicinity of a thrombus site.

19 Claims, 9 Drawing Sheets

DEVICES AND METHODS FOR PERFUSION THERAPY

RELATED APPLICATIONS

The present application claims priority to U.S. Provisional Patent Application Ser. No. 61/150,783, entitled "Devices and Methods for Perfusion Therapy," by Baxter et al., filed on Feb. 8, 2009; and Ser. No. 61/263,790, entitled "Devices and Methods for Perfusion Therapy," by Baxter et al., filed on Nov. 23, 2009; the full disclosures of which is incorporated herein by reference.

BACKGROUND

The present invention is directed to perfusion devices and methods, in particular to devices and methods for cerebral perfusion therapy, including those for use in the treatment of acute ischemic stroke.

All publications, patents, and published patent applications referred to herein are incorporated herein by reference in their entirety.

SUMMARY

Stroke is one of the most devastating medical conditions our society faces. The American Heart Association reports that stroke occurs every 45 seconds, accounting for 1 in 16 deaths, with about 750,000 cases in the United States in 2008. It is the second leading cause of death worldwide and the number one reason for nursing home admissions each year in the United States. It can affect individuals at any age, including the very young.

Stroke occurs when the arteries leading to, or within, the brain become interrupted. Such a blood vessel may become blocked (ischemic stroke) or may rupture (hemorrhagic stroke). Ischemic stroke, caused by blockage of blood flow, is the most common type of stroke. Once the brain is deprived of blood, and thereby the oxygen which it carries, affected brain tissue becomes dysfunctional and ever increasing, potentially irreversible, tissue damage ensues.

Stroke represents a medical emergency and is a potentially reversible process. When large vessels are involved, stroke may be associated with the irreversible destruction of approximately one hundred and twenty million neurons each hour the obstructing lesion ("thrombus") goes untreated. Rapid reperfusion and removal of the thrombus is critically important. The obstructing lesion that interrupts the carotid arterial or cerebral arterial circulation may originate from below the brain, such as in the heart, or form in situ within the arterial circulation itself. Large vessel strokes most frequently involve the territory of the Middle Cerebral artery. Shortly after a thrombus interrupts blood flow to a large artery in the brain, the "Core" area of brain tissue, most severely lacking in blood flow, will begin a process of irreversible cell damage. This area is surrounded by a zone ("the Ischemic Penumbra") that eventually will be irreversibly damaged if blood is not restored within short order. The goal of stroke therapy is to provide blood flow to the "Core" and "Penumbral" areas as rapidly as possible. While there are many types of stroke symptoms, indicative of ischemia to these regions, the most common symptoms are sudden numbness or weakness in the face, arm, and/or leg on one side of the body. Rapid symptom recognition and transport to an appropriate hospital is critical so that treatment to reverse this ischemic process can be attempted.

Prior to 1996, no approved treatment to reverse brain ischemia in acute stroke was available. In 1996 the pharmaceutical compound tissue plasminogen activator (t-PA) received approval by the Food & Drug Administration (FDA) for the treatment of acute ischemic stroke. This drug could, in some cases, stop and reverse stroke by dissolving the obstructing thrombus. The benefit of t-PA, however, is limited in that it has significant clinical benefit in only approximately 12% of patients who receive it as therapy for acute ischemic stroke. Furthermore, in the case of ischemic stroke due to obstruction at the level of the large proximal vessels of the brain, i.e., proximal Middle Cerebral Artery, Basilar, or Internal Carotid Artery less than 10% of patients treated benefit significantly. Current FDA restrictions limit utilization of t-PA to administration within three hours from onset of stroke symptom. Furthermore, numerous other exclusion criteria exist such that less than 5% of patients who experience a stroke in the United States actually receive t-PA yearly. Due to an ever increasing number of people over age 65 (and the expected 2.5-fold increase in atrial fibrillation over the next 50 years) a steady rise in the number of strokes due to large vessel embolic occlusions is expected. As the population ages, therefore, not only is the total number of ischemic stroke per year expected to increase but so is the percentage of strokes amenable to endovascular therapies. This underscores the tremendous opportunity to develop a rapid neuro-protectant device whose function is immediate large vessel arterial reperfusion. As the total cost to society of ischemic stroke for the period of 2005 to 2050 was recently projected to be $2.2 trillion the introduction of new technologies to mitigate stroke impact are of the utmost priority.

New devices designed for mechanical thrombectomy in acute ischemic stroke have been approved for use by FDA. One such device, the "MERCI" device ("Mechanical Embolus Removal in Cerebral Ischemia", manufactured by Concentric Medical, Mountain View, Calif.) is used to extracting and removing thrombus from the brain of acute stroke patients. A second endovascular device, operating on the principle of suction (the Penumbra device), has also received FDA approval for use in patients with acute ischemic stroke.

Although FDA approval of t-PA and certain endovascular devices represents a significant advancement in the field of stroke medicine, the majority of patients experiencing large strokes today still demonstrate poor outcomes. Therefore, there still exists a great need for improved devices and methods for rapid cerebral tissue reperfusion for patients experiencing acute ischemic stroke. The present invention, addresses this and many other needs in this area.

SUMMARY

The present invention relates to treatments, devices, systems, and assemblies, which allow for and/or enable the passage of blood, oxygen, lytic therapy, neuroprotectants and thrombectomy devices, directly through or in the vicinity of an obstructing thrombus. The present devices and methods provide sufficient blood flow and oxygenation to help minimize neuronal tissue damage thus enhancing clinical recovery of a stroke patient. In an embodiment, the present devices and methods provide blood and/or oxygen to a target vessel of interest, rapidly reperfusing brain tissue and thereby mitigating the ischemic process and minimizing brain cell death. An important predictor of good outcome in the treatment of such strokes, including treatment with endovascular devices, appears to be time to reperfusion of blood to brain tissue. Extraction of an obstructing thrombus deep within the brain of a stroke patient is a tedious and time consuming process even for highly skilled interventionalists. Numerous endovascular studies demonstrate that endovascular thrombectomy therapy for acute stroke may be a lengthy procedure, with durations often of over one to two hours, during which time brain cells lack critical nutrients essential for viability thereby increasing likelihood of patient morbidity and death. As such, and without intending any limitations, it is believed that the present devices and methods facilitate down-stream blood flow to the brain of patients experiencing acute ischemic stroke for the purpose of enhancing clinical recovery.

In an embodiment, the treatments, and methods, embodying features of the present invention, include the use of a new device and/or system and/or assembly embodying features of the present invention. The present system is referred to as the Neuronal Protection System ("hereafter for purposes of brevity, referred to as "NPS"), including a Neuronal Protection Device ("hereafter for purposes of brevity, referred to as "NPD").

In an embodiment an assembly for perfusion therapy includes a perfusion catheter including an elongate member having proximal and distal ends, proximal and distal portions, an inner lumen extending along at least the distal portion, and a plurality of apertures disposed along the distal portion and extending from an outer surface of the elongate member to the inner lumen. The apertures aid in the delivery of any one or more of blood, therapeutic, diagnostic, or other suitable fluids through the perfusion catheter and/or obturator to or to the vicinity of the thrombus site. The distal end of the perfusion catheter may be tapered in the distal direction. Without intending any limitations, it is believed that the distal taper, in some embodiments, may minimize hemolysis of the blood at the treatment site, as will be further explained below. The tapered distal end may aid in navigating through the thrombus during advancement of the device.

In one embodiment, the assembly further includes an obturator including an elongate member having proximal and distal ends, proximal and distal portions, a lumen extending along at least the distal portion. The obturator is configured for movable disposal adjacent the apertures of the perfusion catheter and to movably at least partially obstruct the apertures. In an embodiment, the obturator is configured for movable disposal within the inner lumen of the perfusion catheter and to movably at least partially obstruct the apertures. The elongate member of the obturator may be a tubular member or a retractable sheath. The obturator may be disposed on the exterior of the perfusion catheter. The blood or other suitable fluids may be directed from the perfusion pump through the inner lumen of the obturator, as when the obturator is disposed within the inner lumen of the perfusion catheter, and through the perfusion catheter aperture to the desired treatment site. In some embodiments where the obturator is disposed on the exterior surface of the perfusion catheter, blood or other suitable fluids may be pumped through the inner lumen of the perfusion catheter.

In an embodiment, the assembly further includes a guide catheter having an inner lumen configured to receive the perfusion catheter therein. The obturator, depending on the design may be disposable within the inner lumen of the perfusion catheter or longitudinally in between the guide catheter and the perfusion catheter (as when the obturator is disposed on the exterior of the perfusion catheter). The assembly may also include a guidewire disposable in the inner lumen of the obturator and/or perfusion catheter to aid in the advancement of the device within the patient's body.

In an embodiment, a perfusion system includes a perfusion catheter including an elongate member having proximal and distal ends, proximal and distal portions, an inner lumen extending along at least the distal portion, and a plurality of apertures disposed along the distal portion and extending from an outer surface of the elongate member to the inner lumen. The apertures aid in the delivery of any one or more of blood, therapeutic, diagnostic, or other suitable fluids through the perfusion catheter and/or obturator to or to the vicinity of the thrombus site. The distal end of the perfusion catheter may be tapered in the distal direction. The system further includes an obturator including an elongate member having proximal and distal ends, proximal and distal portions, a lumen extending along at least the distal portion. The obturator is configured for movable disposal adjacent the apertures of the perfusion catheter and to movably at least partially obstruct the apertures. In an embodiment, the obturator is configured for movable disposal within the inner lumen of the perfusion catheter and to movably at least partially obstruct the apertures. The elongate member of the obturator may be a tubular member or a retractable sheath. The obturator may be disposed on the exterior of the perfusion catheter. The blood or other suitable fluids may be directed from the perfusion pump through the inner lumen of the obturator, as when the obturator is disposed within the inner lumen of the perfusion catheter, and through the perfusion catheter aperture to the desired treatment site. The system further includes a perfusion pump fluidically connectable to either or both the perfusion catheter and obturator and is configured to actively supply blood to a thrombus site through the perfusion catheter/obturator. In some embodiments where the obturator is disposed on the exterior surface of the perfusion catheter, blood or other suitable fluids may be pumped through the inner lumen of the perfusion catheter.

In an embodiment, the blood is provided to the perfusion pump by way of a conduit in fluid communication with the patient's own blood supply. In an embodiment, the blood is delivered from the perfusion pump to the patient under pressure. The blood may be cooled prior to being pumped from the perfusion pump to the patient. The blood pumped to the patient may be hyper-oxygenated such that the patient may receive oxygen, normally up to 100% $FIO_2$. In one embodiment, the hyper-oxygenation of the blood supply from the patient may be done by placing the patient on an external mechanical ventilator, thus providing hyper-oxygenated blood to be perfused via the NPS system.

An embodiment of method for perfusion therapy of a patient includes providing a perfusion device including a perfusion catheter including an elongate member having proximal and distal ends, proximal and distal portions, an inner lumen extending along at least the distal portion, a plurality of apertures disposed along the distal portion and extending from an outer surface of the elongate member to the inner lumen; and an obturator including an elongate member having proximal and distal ends, proximal and distal portions, a lumen extending along at least the distal portion, the obturator configured for disposal adjacent the apertures of the perfusion catheter and to movably at least partially obstruct the apertures. In an embodiment, the obturator is configured for disposal within the inner lumen of the perfusion catheter and to movably at least partially obstruct the apertures. The method further includes providing a perfusion pump fluidically connectable to the perfusion device and configured to actively supply blood to a thrombus site through the perfusion catheter and/or the obturator.

The method further includes advancing intracorporeally the perfusion catheter and the obturator through a patient's artery to a treatment site distal to a thrombus site; retracting the obturator proximally to expose at least a portion of the apertures; and pumping blood from the perfusion pump through the perfusion catheter and/or obturator to a treatment site distal to the thrombus site.

In an embodiment of a method, the obturator is disposed within the inner lumen of the perfusion catheter prior to advancement within the patient's body. The obturator may be moved proximally within the perfusion catheter lumen to at least substantially obstruct the apertures which are within the thrombus area prior to delivering blood and/or therapeutic and/or diagnostic fluids from the pump to the treatment site.

The blood may be cooled prior to being pumped into the patient. Blood may be supplied from the patient's own blood supply to the perfusion pump. This supplied blood may be withdrawn from the patient real time during the performance of the procedure. The blood pumped to the patient may be hyper-oxygenated such that the patient may receive oxygen, normally up to 100% $FIO_2$. In one embodiment, the hyper-oxygenation of the blood supply from the patient may be done by placing the patient on an external mechanical ventilator, thus providing hyper-oxygenated blood to be perfused via the NPS system.

In an embodiment, the method further includes revascularizing the thrombus site. The revascularization may be performed by advancing an endovasulcar thrombectomy device through the perfusion catheter and/or obturator and performing a thrombectomy procedure.

The method may be cerebral perfusion therapy, and particularly to treat ischemic stroke.

The drawings illustrate embodiments of the invention and are not limiting. For clarity and ease of illustration, the drawings are not made to scale and, in some instances, various aspects may be shown exaggerated or enlarged to facilitate an understanding of particular embodiments.

DESCRIPTION

Figure 1:
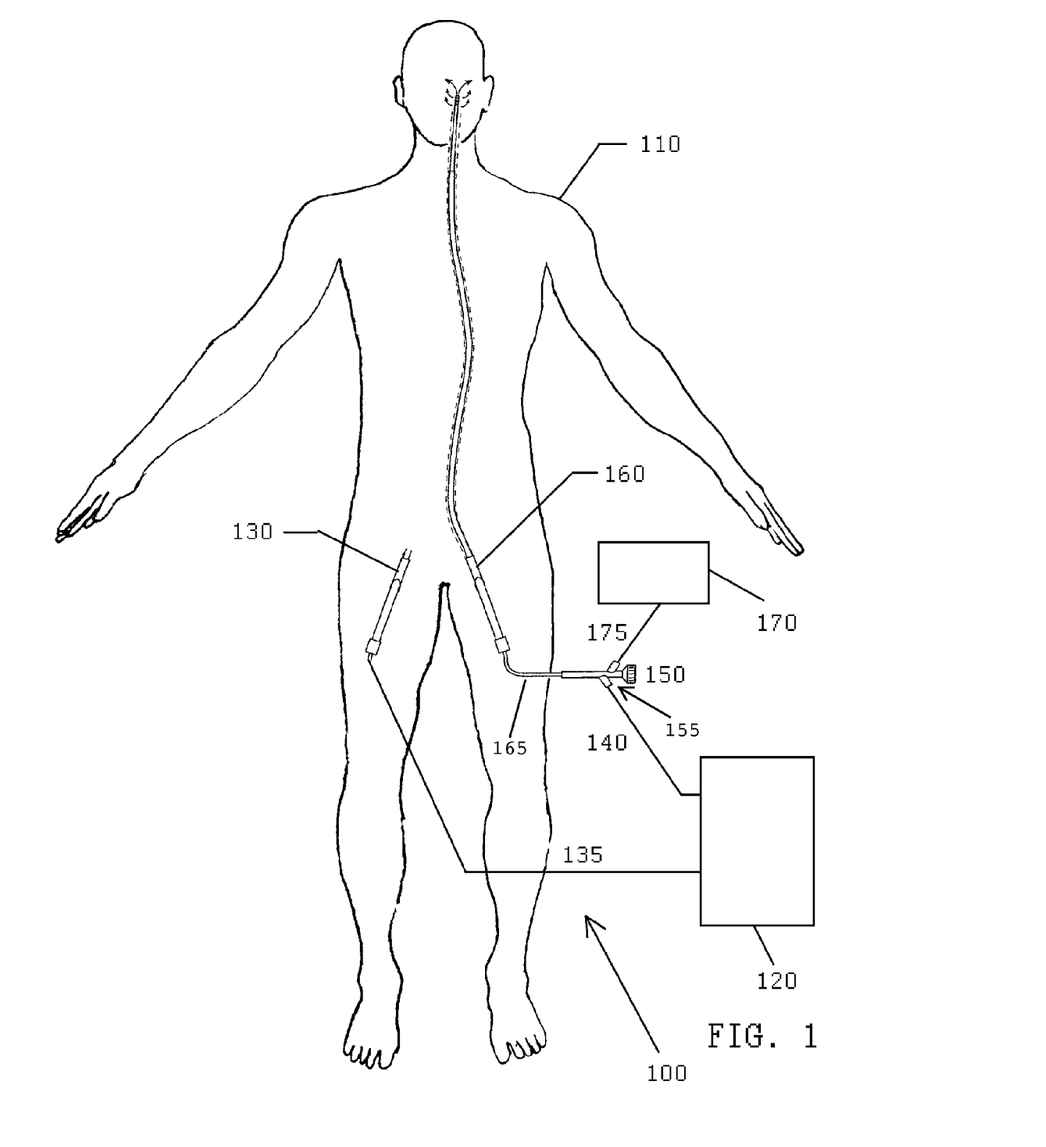
FIG. 1 is an illustration of a neuronal protection system embodying features of the present invention and as in use with a patient.

Referring to FIG. 1, an assembly 100 embodying features of the present invention is shown as set up for treating a patient 110. As shown, the assembly 100 includes a perfusion pump 120 in fluidic communication with an output femoral sheath 130 and connector 135. The Connector 135 enables movement of blood from the femoral arterial sheath which is insertable into one of the femoral arteries of the patient by being attached to the perfusion pump.

A connector 140 fluidically connects the perfusion pump 120 through port 150 of a hemostatic valve 155 to an input femoral artery sheath, 165 through connector 165. A source 170 of therapeutic and/or diagnostic fluid is also in fluid communication with the perfusion device through port 175 of the valve 155.

Figures 2, 2A, 2B:
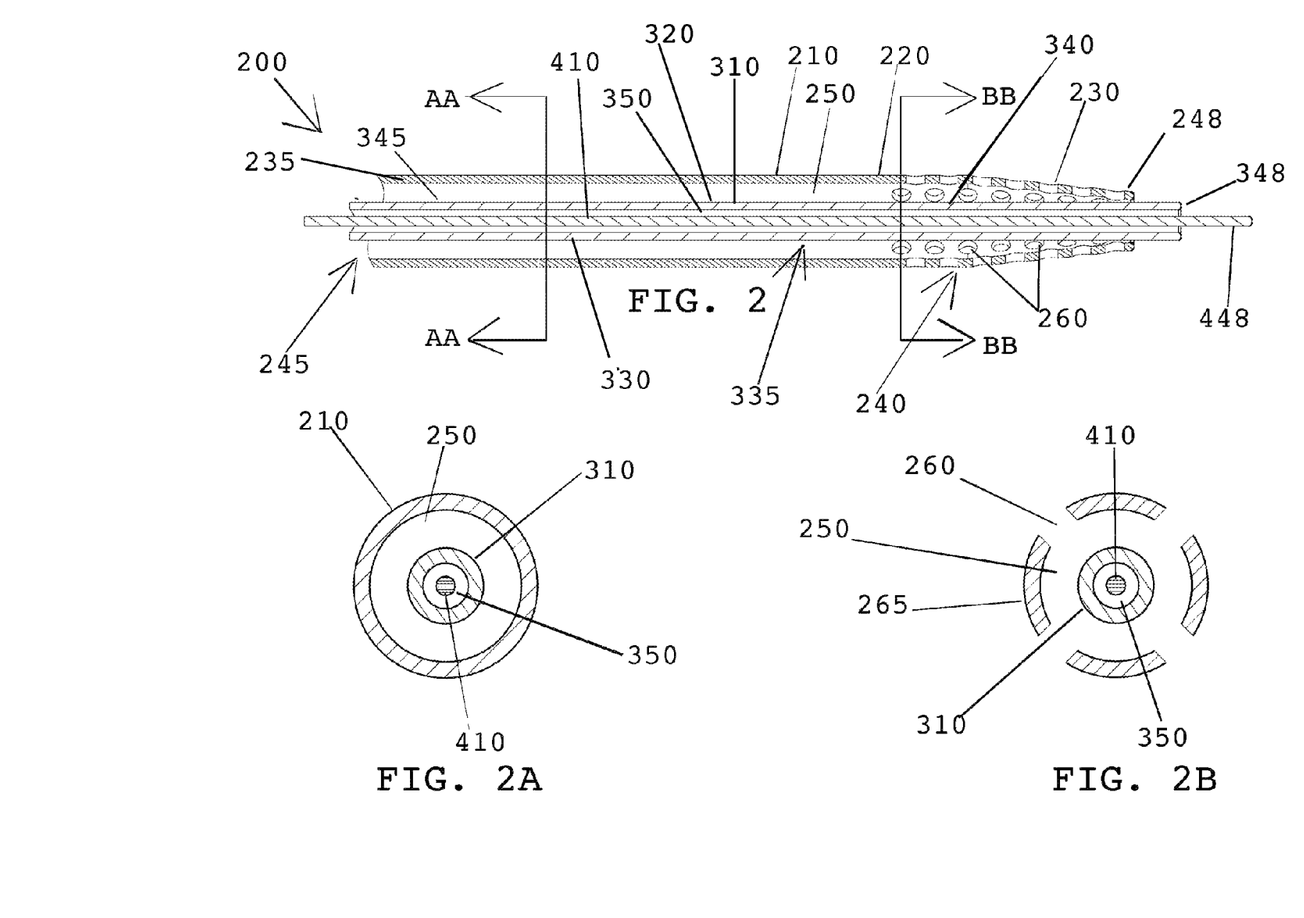
FIG. 2 is an illustration of a neuronal protection device embodying features of the present invention and including a perfusion catheter and obturator with a guidewire disposed therein.
FIGS. 2A and 2B, are cross sectional views of the device of FIG. 2 taken along cross-sections AA and BB, respectively.

Now referring to FIGS. 2, 2A, and 2B, a neuronal protection device 200, embodying features of the present invention is shown, including a perfusion catheter 210 including an elongate member such as a tubular member 220 having distal and proximal ends, 230 and 235, distal and proximal portions, 240 and 245, and distal tip 248. An inner lumen 250 extends longitudinally at least along the distal portion of the perfusion catheter. The distal portion includes one or more apertures 260 extending from an outer surface 265 of the perfusion catheter to the perfusion catheter inner lumen 250. The apertures aid in the delivery of any one or more of blood, therapeutic, diagnostic, or other suitable fluids through the perfusion catheter and/or an obturator to or the vicinity of the thrombus site.

In an embodiment, the distal end 230 of the perfusion catheter is distally tapered. Without intending any limitations, it is believed that the distal taper, in some embodiments, may minimize hydrolysis of blood during the treatment, as will be further explained below. The tapered distal end also aids in navigating through the thrombus during advancement of the device 200. In an embodiment, the tapered distal end assists with minimizing the hemolysis of the blood at the treatment site.

An obturator 310, as shown, is disposed inside at least a portion of the inner lumen 250 of the perfusion catheter 210. The obturator 310 includes an elongate member such as a tubular member 320 having distal and proximal ends, 340 and 345, distal and proximal portions, 335 and 330, and a distal tip 348. An inner lumen 350 extends longitudinally at least along the distal portion of the obturator. As shown, the distal end of the obturator extends into the distal portion of the perfusion catheter and extends distally beyond the perfusion catheter distal end. The blood or other suitable fluids may be directed from the perfusion pump through the inner lumen of the obturator, as when the obturator is disposed within the inner lumen of the perfusion catheter, and through the perfusion catheter apertures to the desired treatment site, or through obturator's distal tip 348.

A guide wire 410, as shown, is disposed in the inner lumen 350 of the obturator 310, with a distal tip 448 of the guide wire 410 extending distal of the distal tip 248 of the perfusion catheter 210 and the distal tip 348 of the obturator.

Figures 3, 3A, 3B:
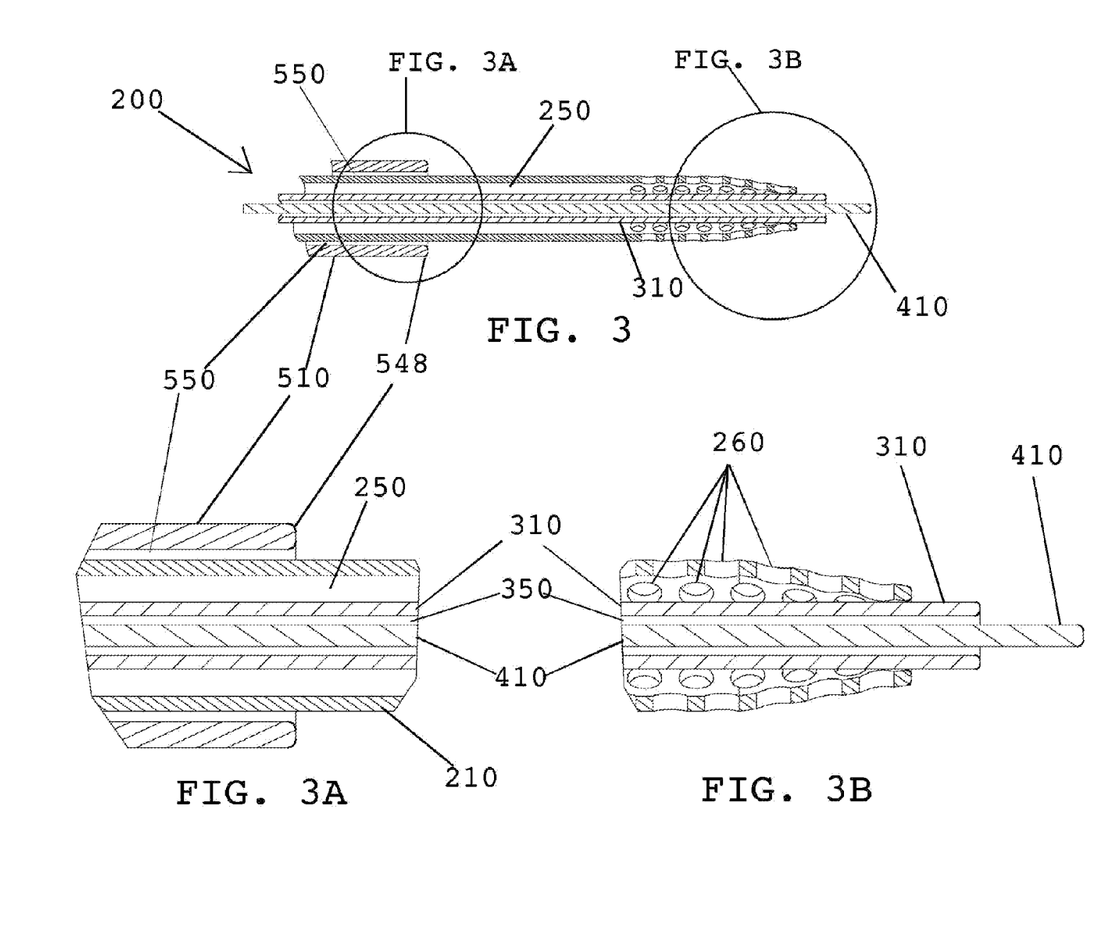
FIG. 3 is an illustration, partially cut away, of the neuronal protection device of FIG. 2.
FIGS. 3A and 3B, are exploded views of portions of the proximal and distal portions of the device of FIG. 2, respectively.

Now referring to FIGS. 3, 3A and 3B, the device 200 is shown disposed in an inner lumen 550 of a guide catheter 510, and extending distally from a distal tip 548 of the guide catheter.

The perfusion catheter and obturator may be designed and constructed to meet the necessary requirements of the anatomy. In an embodiment, some of the components, construct, size, and material of the perfusion catheter and obturator may be similar to those used in delivering the MERCI device into the brain, the details of which are incorporated herein by reference. In some embodiments, the perfusion catheter may normally have an internal diameter ranging from about 1.0 mm to about 1.5 mm; with the perfusion catheter distal tip, when tapered, having a length ranging from about 15 mm to 30 mm. The aperture size for the perfusion catheter typically ranges from about 0.1 mm to about 0.5 mm. The typical catheter lengths for the perfusion catheter are in the 135 cm range and for the obturator, the 150 cm range.

In embodiments of methods of treatment embodying features of the present invention, one or more of the following steps may be utilized, as deemed necessary by the practitioner:

Typically, a patient exhibiting a stroke will be evaluated emergently by a medical stroke expert. A computerized tomography (CT) scan of the brain is performed to confirm that the stroke is ischemic, not hemorrhagic, and to assist in localization of the obstructing thrombus. The stroke specialist will determine if the thrombus is located within an artery supplying the brain and whether the thrombus is amenable to endovascular extraction by an interventionalist physician (as for example by using the MERCI or Penumbra device). If the patient is deemed an appropriate candidate for the procedure, the patient may undergo a standard intubation procedure (i.e., placed on a ventilator) for airway protection and to facilitate hyper-oxygenation. The patient may receive oxygen at an $FIO_2$ of up to 100%. The patient is then brought to the endovascular suite. Arterial access is gained by placement of a short femoral arterial sheath 130 (FIG. 1). A sheath that is large enough to allow blood withdrawal around the guide catheter/perfusion catheter may be selected or the operator may choose to place a second sheath 160 in the contralateral femoral artery that is for the purposes of blood delivery to the perfusion pump (FIG. 1). The blood is delivered to the perfusion pump via Connector 135.

In exemplary embodiment of a method embodying features of the present invention, thereafter, using standard angiographic technique, a guide catheter 510 will be inserted by way of the femoral sheath 160 and advanced through the aorta into one of the larger cervical arteries (the Carotid or Vertebral arteries) that supplies the occluded vessel at the base of the brain. A liquid "contrast" material is pumped through the guide catheter (an angiogram), to determine exactly where the occluding thrombus is located.

Figure 4:
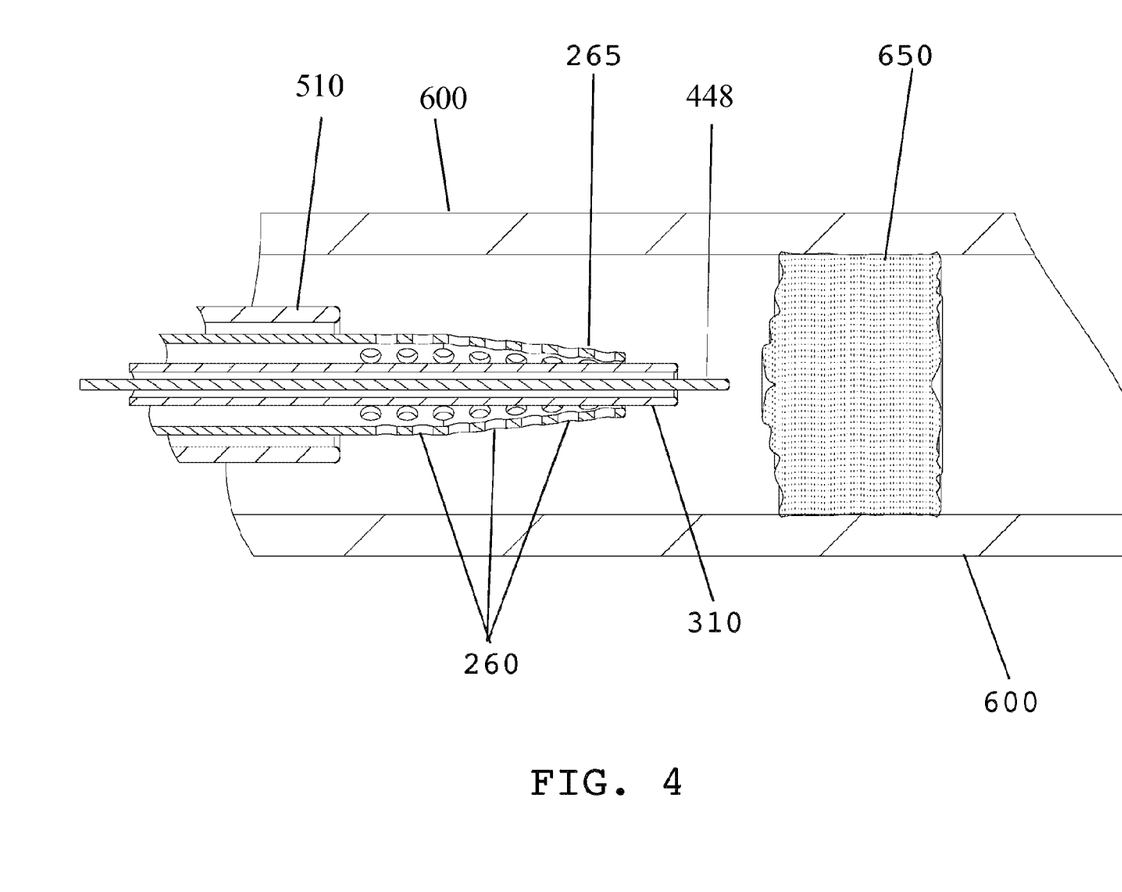
FIG. 4 is an illustration of the perfusion device of FIG. 2 disposed in a patient's lumen proximal to a thrombus site.
Figure 5:
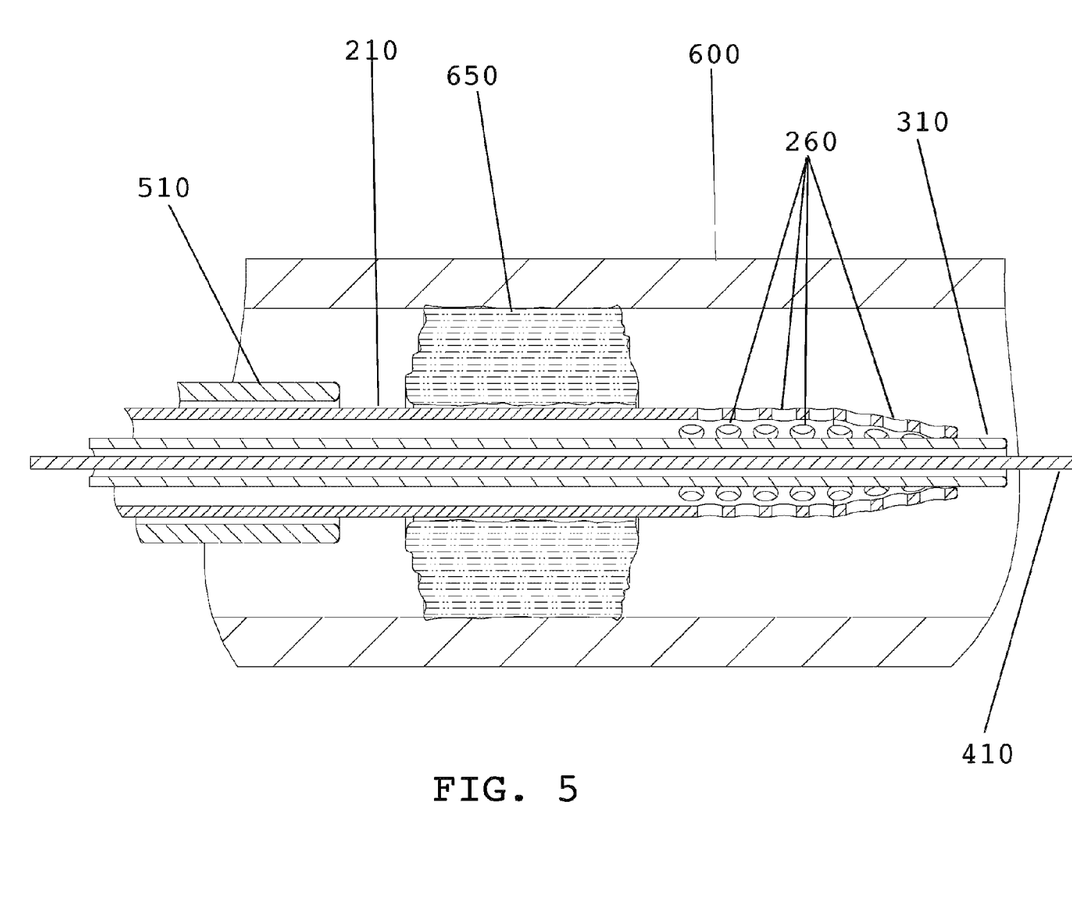
FIG. 5 is an illustration of the perfusion device of FIG. 4 disposed in a patient's lumen with the perfusion device distal portion disposed distal to a thrombus site.
Figure 6:
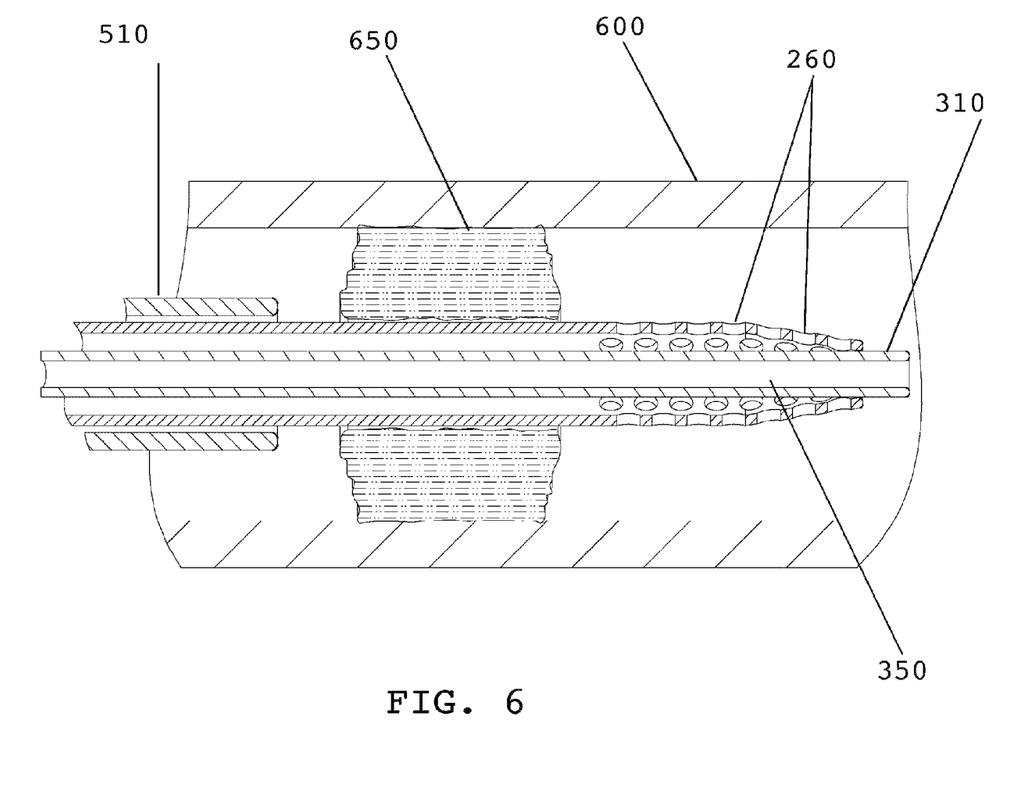
FIG. 6 is an illustration of the perfusion device of FIG. 5 with the guidewire removed.
Figure 7:
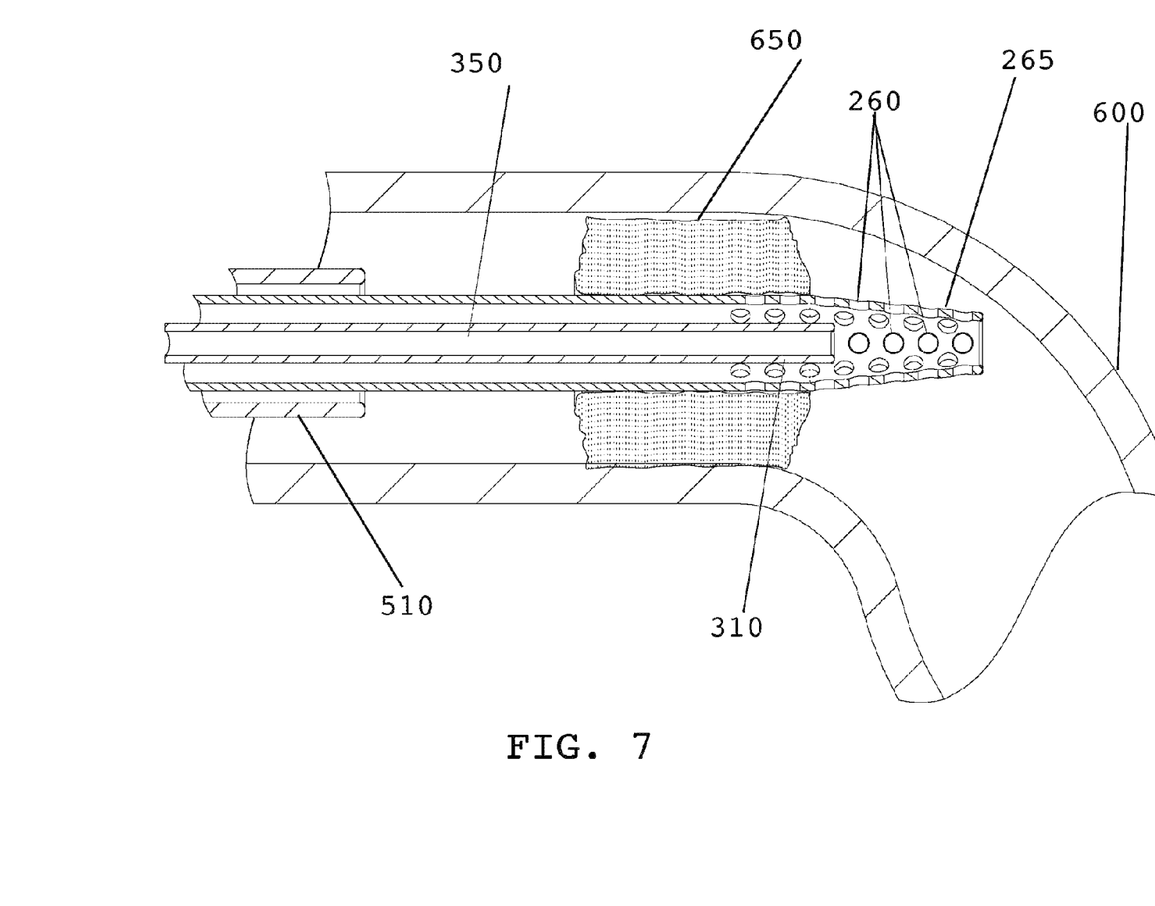
FIG. 7 is an illustration of the perfusion device of FIG. 5 with the only a portion of perfusion apertures disposed distal to the thrombus.
Figure 8:
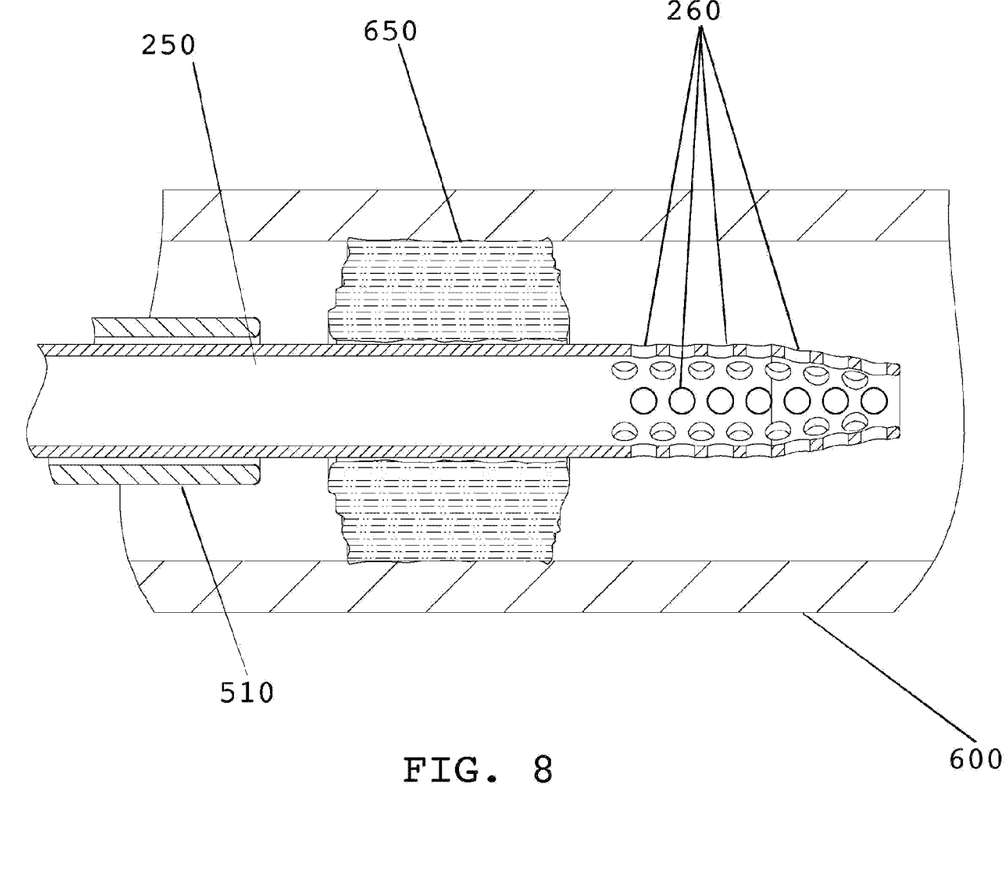
FIG. 8 is an illustration of the perfusion device of FIG. 2 with the obturator removed from a guide catheter.

It should be appreciated by those skilled in the art, that the methods embodying features of the present invention, as described herein, may include any one or more of such steps not necessarily being described. Outside of the patient's body, the perfusion catheter 210 and obturator 310 are prepared for delivery by placing a rotating hemostatic valve (RHV) at the proximal end for continuous infusion of heparinized saline. The guide wire 410 is placed in the lumen 350 of the obturator 310 and this obturator/guide wire unit is then advanced through the inner lumen 250 of the perfusion catheter 210 until the tip of the obturator/guide wire extends distal to the distal tip 248 of the perfusion catheter. In some embodiments, the obturator may serve as a platform for delivery of thrombectomy devices/lytics and/or therapeutic and/or diagnostic fluids, if desired. In an embodiment, this entire catheter combination (perfusion catheter/obturator/guide wire) is then introduced through the guide catheter 510 and advanced to the target vessel 600 using standard microcatheter techniques, as partially shown in FIG. 4. The tips of perfusion catheter/obturator/guidewire are advanced distal to the obstructing thrombus 650, as shown in FIG. 5. The guidewire is thereafter removed (See FIG. 6). It may be desirable to confirm that the perfusion catheter tip is located distal to the thrombus by injecting a small amount of contrast. In an embodiment in the case that only a segment of the entire length of perfusion apertures are exposed distal to the thrombus, the obturator may be used to deliver blood flow. The obturator tip is withdrawn proximally to expose the perfusion apertures. In an embodiment, as shown in FIG. 7, the obturator tip is withdrawn proximally to expose the maximum number of perfusion apertures that are distal to the thrombus while continuing to cover (e.g., disposed adjacent the apertures so as to minimize flow of blood or other therapeutic/diagnostic fluids pumped or delivered through the perfusion catheter/ obturator) the perfusion apertures that are at the level of or proximal to the thrombus. The obturator is then attached to the perfusion pump and perfusion is initiated with blood flow being directed to the apertures distal to the thrombus. In the case that the landing area in the artery allows exposure of the entire length of the aperture section, then the obturator may be removed and the perfusion catheter is attached to the perfusion pump and perfusion is initiated (See FIG. 8).

In an embodiment, thrombolytic agents may be used to enhance the treatment. In an embodiment, a sufficiently effective small quantity of contrast is injected through the device to demonstrate the distal end of the thrombus. Standard angiographic run is performed through the guide catheter to outline the proximal end of the thrombus. The obturator is withdrawn to expose the maximum number of perfusion apertures of the perfusion catheter. The thrombolytic agent is thereafter introduced into the desired area.

In an embodiment, it may be desirable to perform intra-arterial mechanical thrombectomy. In an embodiment, a sufficiently effective small quantity of contrast is injected to confirm that the NPS catheter tip is distal to the thrombus. A thrombectomy device is introduced through the obturator/PC combination and thrombectomy is performed according to device procedural guidelines, all of which by example are incorporated herein by reference (Mechanical Embolus Removal in Cerebral Ischemia", manufactured by Concentric Medical, Mountain View, Calif.).

In an embodiment, the thrombus may have a length ranging from about 1 cm to about 18 cm. The artery "Landing Area" beyond the thrombus generally has a vessel diameter range from about 1.5 mm to about 2.5 mm with the thrombosed artery generally ranging from about 2.5 mm to about 4.0 mm in diameter.

The perfusion pump is similar to those used in pumping blood through the cardiac arteries during heart surgery, the details of which are incorporated herein by reference, with the additional inventive features described herein and further below.

In an embodiment, the perfusion pump incorporates a volumetric displacement pump configured to provide pressure controlled delivery of oxygenated blood at flow rates necessary to support the affected region of the brain distal to an arterial occlusion through a micro-catheter at pressures above 1,000 mm Hg. In an embodiment, the pump mechanism is a dual chamber piston pump; although, if non-continuous flow is acceptable a single chamber system could be adapted. In an embodiment, additional high pressure single-chamber pump(s) that contribute neuroprotective agent(s) to the perfusate may be used. The system may also incorporate a perfusate temperature control system to either maintain normothermia or hypothermia to reduce metabolism and aid in recovery and the mitigation of reperfusion injury. In an embodiment, the hardware of the integrated system interfaces with a sterile disposable delivery set that contains the conduits for carrying arterialized blood from the patient to the neuro-perfusion system and then to the micro catheter.

Also contained within the sterile disposable delivery set are pump cassettes that interface with the piston pumps. The sterile disposable are pump may include cassettes that interface with the piston pumps. A heat transfer device may be sued to serve as the medium for transferring heat energy to and from the perfusate. Safety devices and components including emboli detectors may further be employed. The maximum pump pressure as compared to cardiac pumps is modified to allow for pumping of blood up the perfusion catheter so that blood may be delivered distal to the thrombus perfusing the ischemic brain tissue at an appropriate flow rate range of 50 to 150 ml/min.

By placing the patient on an external mechanical ventilator the patient may receive oxygen at up to 100% $FIO_2$ thus providing hyper-oxygenated blood to be perfused via the NPS system. As seen in FIG. 1, the blood moves out of the patient's body (through the sheath in the patient's femoral artery or from a second access site), through connector 135 to the perfusion pump. The pump then delivers the blood to the perfusion catheter via connector 140. In an embodiment, the perfusion pump may also cool the blood, a technique called "hypothermia." Without intending any limitations, it is believed that the cooling of the patient's blood may have a "neuro-protective effect" on the brain that delays the destruction of brain cells until blood flow is restored. The perfusion pump may also be used to add other suitable drugs to the blood, such as, but not limited to chemical "neuro-protectants" that may be of benefit when delivered directly to the stroke brain tissue.

In an embodiment, the obturator takes on the form of a retractable sheath disposable within the inner lumen of the perfusion catheter. In this embodiment, a distal end of the obturator may be proximally retractable by suitable means such as a wire connected to the obturator distal end, with a proximal end of the wire extending proximally from the proximal end of the perfusion catheter. In this configuration, the apertures are covered (or fluid flow may be at least partially obstructed) by the sheath and may be exposed, as desired, by retracting the sheath proximally by way of the wire. Alternatively, the sheath may be disposable over the exterior surface of the perfusion catheter and is retractable by suitable means such as wire. In another embodiment, the obturator may be a tubular member disposable over the exterior surface of the perfusion catheter. Retraction of the obturator in the proximal direction exposes the apertures for fluid delivery.

Below, are exemplary applications of the NPS devices and methods embodying features of the present invention. In first exemplary application, embodying features of the present invention, as discussed above, the NPS will be utilized as a reperfusion platform for carrying out an endovascular acute stroke procedure targeted at medium to large vessel occlusions. NPS reperfusion will be implemented at the start of the procedure to achieve instantaneous reperfusion to facilitate and restore normal oxygen levels in the ischemic penumbra thereby minimizing permanent neuronal damage. Once the initial NPS tissue rescue reperfusion step is complete, a revascularization method can be employed to obtain permanent vessel patency. If such revascularization involves utilization of a MERCI, Penumbra, or other similar devices, the NPS platform will allow that device to be inserted within and through the NPS for attempting the thrombectomy portion of the procedure. Thrombus extraction may then be performed as needed. As thrombectomy procedures often require use of multiple types of devices over several hours, continuous or cyclical NPS tissue rescue reperfusion may be utilized adjunctively during the endovascular procedure. As it is recognized that acute ischemic stroke is heterogeneous (carotid versus intracranial; embolic versus medium to large vessel in situ atherosclerotic disease), this first exemplary application of the NPS provides a general platform for neuronal rescue from which a number of therapies can be performed (including but not limited to intravenous/intra-arterial pharmacological thrombolysis, mechanical thrombus removal, stenting, or other forms of neuroprotection).

Yet it is recognized that a significant percentage of clinically devastating strokes involve vessels which due to size or location are not amenable to mechanical clot extraction (for example, lacunar stroke, distal branch MCA thrombus, etc.). In a second exemplary application, embodying features of the present invention, includes utilization of the NPS to provide neuronal protection via augmentation of collateral arterial flow (increased tissue oxygenation and egress of cytotoxic compounds), and/or localized delivery of hypothermia or other neuroprotectant directly to the ischemic vascular bed. It should be recognized that this second exemplary application may be used in conjunction with other intravenous thrombolytic or neuroprotectant therapies.

It is recognized that many acute stroke patients initially are directed to hospitals where advanced stroke care is not available. A third exemplary application embodying features of the present invention, the NPS involves its use as a generalized neuronal protection bridging device in which NPS therapy is initiated at the first responder hospital and maintained during transport to a hospital which offers the full complement of acute stroke treatment options.

In order to assess the feasibility of the devices and methods of the present invention, certain experiments were performed and data collected. This data is presented by way of example and not limitation. By way of explanation and not limitation, it is believed, that that blood flow rates in the range of about 50-150 ml/min through the catheters of the present invention into the large arteries of the brain are desired to normalize oxygen levels in the tissue. Using two catheters (a small Concentric 18 L and the larger DAC), it was demonstrated, as shown in Table I below, that the present method was successful in obtaining flow rates with saline above 200 ml/min using the larger DAC catheter. This data demonstrate the feasibility of achieving the goals of the NPS. Data were generated utilizing a perfusion pump with the characteristics described above.

TABLE I

Initial Saline Pressure-Flow Test Results Using Two Concentric. Micro-catheters

|  | Pressure (mm HG) | Flow (ml/min) |
|---|---|---|
| Catheter 1 - MC-18L (ID = 0.019 in) | 500 | 4 |
|  | 1100 | 15 |
|  | 1400 | 18 |
| Catheter 2 - DAC (4.3F OD-3.3F ID ID = 0.044 in) | 500 | 88 |
|  | 1100 | 165 |
|  | 1400 | 265 |

Figure 9:
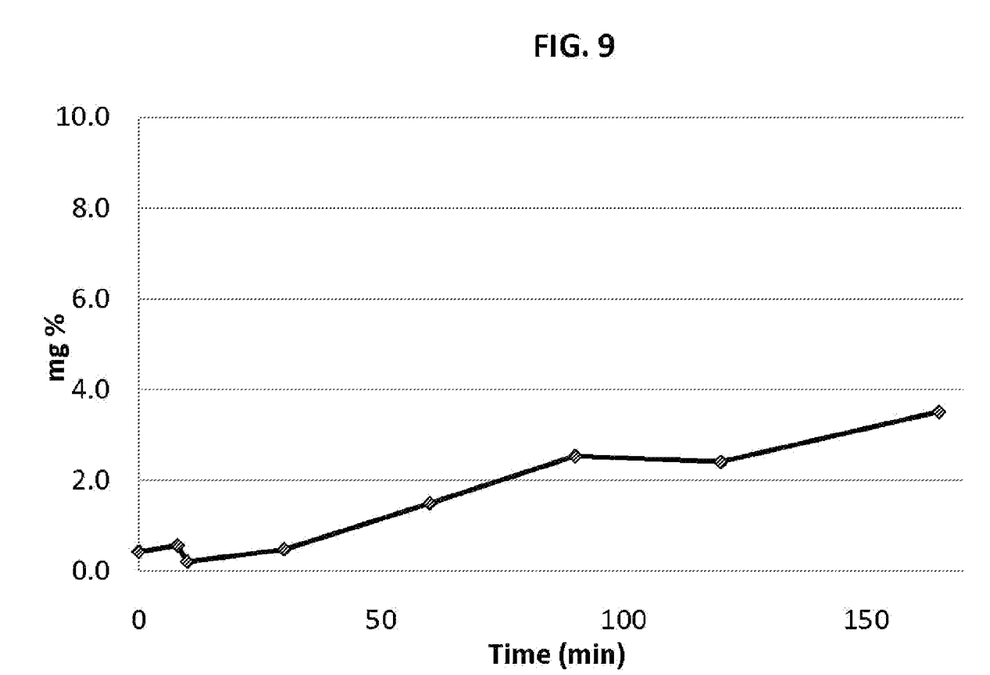
FIG. 9 is a graphical representation of the data presented in TABLE II.

When a similar feasibility study was performed using whole human blood similar results were obtained despite the introduction of increased viscosity. As demonstrated in Table II, a physiological relevant human blood flow rate of above 100 ml/min through a Concentric DAC microcatheter could be maintained without significantly increasing pump pressure. Furthermore, when hemolysis of whole human blood was analyzed by measuring free Hemoglobin levels during recurrent circulation though the NPS (as performed to generate the results presented FIG. 9), no significant erythrocyte hemolysis was noted. The human blood pressure-flow and hemolysis data presented in TABLES I and II were generated utilized a pump with the characteristics described above.

TABLE II

Pressure-Flow Test Results Using
Concentric DAC Micro-catheter
Pressure Drop Data with Blood

| Flow Rate (ml/min) | Sys Pressure (mm HG) | Temperature (° C.) |
|---|---|---|
| 0 | 78 | 36 |
| 25 | 287 | 36 |
| 50 | 482 | 37 |
| 100 | 1031 | 37 |
| 120 | 1135 | 37 |

FIG. 3 indicates that at the physiologically relevant blood flow rates anticipated to be generated by the NPS significant hemolysis does not occur and oxygen carrying capacity is not compromised.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although embodiments of the invention have been described in substantial detail with reference to one or more specific embodiments, those of ordinary skill in the art will recognize that changes may be made to the embodiments specifically disclosed in this application, yet these modifications and improvements are within the scope and spirit of the invention.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this invention.

Certain embodiments of the invention are set forth in the claim(s) that follow(s).

That which is claimed:

1. An assembly for cerebral perfusion therapy, including:
    an outer catheter configured for cerebral perfusion therapy and including
        a single lumen first elongate member having a proximal portion with a proximal end, a distal portion with a distally tapered distal end and an open distal tip, the tapered distal end configured to facilitate navigating the outer catheter into the cerebral circulation and traversing clots within vessels within the brain, an inner lumen extending along at least the distal portion, a plurality of apertures disposed along the distal portion and extending from an outer surface of the first elongate member to the first elongate member inner lumen; the outer catheter being further configured for perfusion of fluids including any one or more of blood, therapeutic agents, diagnostic agents, lytic solutions, and the like; through or in the vicinity of an obstructing cerebral thrombus; and
    An inner catheter configured for use in cerebral perfusion therapy and including
        a second elongate member having a proximal portion with a proximal end, a distal portion with a distal end and an open distal tip, a lumen extending along at least the distal portion, the inner catheter configured for slidable coaxial advancement within the inner lumen of the outer catheter and slidable disposal at any one or more locations, proximal, adjacent, or distal; to at least a portion of the apertures; the inner catheter further being configured for extending distally from the open distal tip of the outer catheter.

2. A device according to claim 1, wherein the inner catheter is configured for slidably, to at least partially obstruct, at least a portion of the apertures, when the inner catheter is disposed in the inner lumen of the outer catheter enabling the distal flow of fluids through the open distal tip of the outer catheter to a treatment site distal to the thrombus.

3. A device according to claim 2, wherein the inner catheter is further configured for delivery of either or both fluids including blood, therapeutic agents, diagnostic agents, lytic solutions and the like; and delivery of treatment devices including thrombectomy devices; to or in the vicinity of the obstructing thrombus.

4. A device according to claim 3, further including a guide catheter having an inner lumen configured to receive the outer catheter therein.

5. A system for cerebral perfusion therapy, including:
    A cerebral perfusion device including
        an outer catheter configured for cerebral perfusion therapy and including a single lumen first elongate member having a proximal portion with a proximal end, a distal portion with a distally tapered distal end and an open distal tip, the tapered distal end configured to facilitate navigating the outer catheter into the cerebral circulation and traversing clots within vessels within the brain, an inner lumen extending along at least the distal portion, a plurality of apertures disposed along the distal portion and extending from an outer surface of the first elongate member to the first elongate member inner lumen; the outer catheter being further configured for perfusion of fluids including any one or more of blood, therapeutic agents, diagnostic agents, lytic solutions, and the like; through or in the vicinity of an obstructing cerebral thrombus; and
    An inner catheter configured for use in cerebral perfusion therapy and including a second elongate member having a proximal portion with a proximal end, a distal portion with a distal end and an open distal tip, a lumen extending along at least the distal portion, the inner catheter configured for slidable coaxial advancement within the inner lumen of the outer catheter and slidable disposal at any one or more locations, proximal, adjacent, or distal; to at least a portion of the apertures; the inner catheter further being configured for extending distally from the open distal tip of the outer catheter; and
    A perfusion pump fluidically connectable to the cerebral perfusion device and configured to actively supply blood to or to a vicinity of a thrombus site through the perfusion device.

6. A system according to claim 5, wherein the inner catheter is configured for slidably, to at least partially obstruct, at least a portion of the apertures, when the inner catheter is disposed in the inner lumen of the outer catheter enabling the distal flow of fluids through the open distal tip of the outer catheter to a treatment site distal to the thrombus.

7. A system according to claim 6, wherein the blood delivered to the patient through the cerebral perfusion device is hyper-oxygenated prior to delivery to the patient's cerebral vessels by way of an external ventilator.

8. A method for cerebral perfusion therapy of a patient, including:
Providing a cerebral perfusion device including
an outer catheter configured for cerebral perfusion therapy and including a single lumen first elongate member having a proximal portion with a proximal end, a distal portion with a distally tapered distal end and an open distal tip, the tapered distal end configured to facilitate navigating the outer catheter into the cerebral circulation and traversing clots within vessels within the brain, an inner lumen extending along at least the distal portion, a plurality of apertures disposed along the distal portion and extending from an outer surface of the first elongate member to the first elongate member inner lumen; the outer catheter being further configured for perfusion of fluids including any one or more of blood, therapeutic agents, diagnostic agents, lytic solutions, and the like; through or in the vicinity of an obstructing cerebral thrombus; and
an inner catheter configured for use in cerebral perfusion therapy and including a second elongate member having a proximal portion with a proximal end, a distal portion with a distal end and an open distal tip, a lumen extending along at least the distal portion, the inner catheter configured for slidable coaxial advancement within the inner lumen of the outer catheter and slidable disposal at any one or more locations, proximal, adjacent, or distal; to at least a portion of the apertures; the inner catheter further being configured for extending distally from the open distal tip of the outer catheter;
Providing a perfusion pump fluidically connectable to the cerebral perfusion device and configured to actively supply blood to a treatment site through the outer catheter or the inner catheter;
Advancing intracorporeally the outer catheter and the inner catheter through a patient's artery to a treatment site distal to a distal edge of the thrombus site;
Retracting the inner catheter proximally to expose at least a portion of the apertures which are distal to the distal edge of the thrombus site; and
Pumping blood from the perfusion pump through either the outer catheter or the inner catheter to the treatment site distal to the thrombus site, through any one or more of the open distal tip of the outer catheter, the open distal tip of the inner catheter, and any unobstructed apertures.

9. A method according to claim 8, wherein the inner catheter at least substantially obstructs the apertures which are within or proximal to the thrombus area prior to delivering fluids from the pump to the treatment site which is distal to the thrombus.

10. A method according to claim 8, wherein the blood delivered to the patient through the cerebral perfusion device is hyper-oxygenated prior to delivery to the patient's cerebral vessels by way of an external ventilator.

11. A method according to claim 8, further including advancing a revascularizing device including an endovascular thrombectomy device through the inner lumen of the inner catheter and revascularizing the thrombus site.

12. A method according to claim 11, wherein the revascularization step includes advancing an endovascular thrombectomy device through the inner catheter and performing a thrombectomy procedure.

13. A method according to claim 12, wherein the method is to directly treat ischemic stroke.

14. A method for cerebral perfusion therapy of a patient, including:
Providing a perfusion device including
An outer catheter including an elongate member having proximal and distal ends, proximal and distal portions, an inner lumen extending along at least the distal portion, a plurality of apertures disposed along the distal portion and extending from an outer surface of the elongate member to the inner lumen; and
An inner catheter including an elongate member having proximal and distal ends, proximal and distal portions, a lumen extending along at least the distal portion, the inner catheter configured for slidable disposal within the inner lumen of the outer catheter and further configured for slidable disposal adjacent at least a portion of the apertures and further configured to slidably at least partially obstruct at least a portion of the apertures; the inner catheter further configured to be disposed at least partially within the inner lumen of the perfusion catheter during an advancing step;
Providing a perfusion pump fluidically connectable to the perfusion device and configured to actively supply blood to a treatment site through the outer catheter or the inner catheter;
Advancing intracorporeally the outer catheter and the inner catheter through a patient's artery to a treatment site distal to a thrombus site;
Retracting the inner catheter proximally to expose at least a portion of the apertures; and
Pumping blood from the perfusion pump through the outer catheter or the inner catheter to the treatment site distal to the thrombus site.

15. A method according to claim 8, wherein the inner catheter substantially obstructs the apertures of the outer catheter which are within or proximal to the thrombus.

16. A method according to claim 8, wherein the inner catheter substantially obstructs fluid flow from all the apertures.

17. A method according to claim 8, further including retracting the inner catheter proximally to expose at least a portion of the apertures of the outer catheter which are distal to the distal edge of the thrombus, the method further including perfusion of the fluid to the treatment site which is distal to the distal edge of the thrombus by way of any one or more of the unobstructed apertures, the open distal tip of the outer catheter, and the open distal tip of the inner catheter.

18. A method according to claim 8, the method further including retracting the inner catheter proximally to remove it from the inner lumen of the outer catheter, the method further including delivering fluids directly through the outer catheter and perfusing fluids including blood into cerebral vessels distal to the thrombus.

19. A method according to claim 8, the method further including perfusion of one or more fluids directly through the outer catheter.

* * * * *